United States Patent
Blanchard et al.

(10) Patent No.: US 6,930,122 B2
(45) Date of Patent: Aug. 16, 2005

(54) USE OF CENTRAL CANNABINOID RECEPTOR ANTAGONIST FOR PREPARING MEDICINES DESIGNED TO FACILITATE SMOKING CESSATION

(75) Inventors: Jean Charles Blanchard, Rue de la Glacière (FR); François Menard, rue du Four (FR)

(73) Assignee: Sanofi-Aventis, Paris (FR)

( * ) Notice: Subject to any disclaimer, the term of this patent is extended or adjusted under 35 U.S.C. 154(b) by 144 days.

(21) Appl. No.: 10/203,077

(22) PCT Filed: Feb. 7, 2001

(86) PCT No.: PCT/FR01/00356

§ 371 (c)(1),
(2), (4) Date: Oct. 15, 2002

(87) PCT Pub. No.: WO01/58450

PCT Pub. Date: Aug. 16, 2001

(65) Prior Publication Data

US 2003/0087933 A1 May 8, 2003

(30) Foreign Application Priority Data

Feb. 9, 2000 (FR) .............................................. 00 01682

(51) Int. Cl.⁷ ........................ A01N 43/50; A61K 31/415
(52) U.S. Cl. ........................ 514/406; 514/326; 514/343; 514/654; 514/813
(58) Field of Search ................................. 514/406, 326, 514/343, 654, 813

(56) References Cited

U.S. PATENT DOCUMENTS

| 5,624,941 A | 4/1997 | Barth et al. |
| 6,344,474 B1 | 2/2002 | Maruani et al. |
| 2002/0128302 A1 * | 9/2002 | Maruani et al. ............ 514/406 |

FOREIGN PATENT DOCUMENTS

| EP | 0 656 354 A | 6/1995 |
| WO | WO 98/32441 A | 7/1998 |
| WO | WO 00/46209 A | 8/2000 |

OTHER PUBLICATIONS

Jorenby et al., A Controlled Trial of Sustained–Release Bupropion, a Nicotine Patch ot Both for Smoking Cessation, 1999, New England Journal of Medicine, vol. 340, No. 9, pp. 685–691.*

Fowler et al., Brian Monoamine Ocidase A Inhibition in Cigarette Smokers, 1996, Proceedings of the National Academy of Science, vol. 93, pp. 14065–14069.*

H. Kobayashi et al., Journal of Toxicological Sciences, vol. 24, No. 1, pp. 1–16, 1999.

F. Rodriguez de Fonseca et al., Acta Pharmacol Sim, vol. 20, No. 12, pp. 1109–1114, 1999.

G.J. Molderings et al., Fundamental Clinical Pharmacology, vol. 12, No. 4, pp. 388–397, 1998.

* cited by examiner

Primary Examiner—Frederick Krass
Assistant Examiner—Amy A. Lewis
(74) Attorney, Agent, or Firm—Balaram Gupta

(57) ABSTRACT

The invention relates to the use of N-piperidino-5-(4-chlorophenyl)-1-(2,4-dichlorophenyl)-4-methylpyrazole-3-carboxamide for helping to quit tobacco consumption.

11 Claims, No Drawings

USE OF CENTRAL CANNABINOID RECEPTOR ANTAGONIST FOR PREPARING MEDICINES DESIGNED TO FACILITATE SMOKING CESSATION

The present invention relates to a novel use of an antagonist of the central cannabinoid receptors, known as the CB1 receptors. More particularly, the invention relates to the use of a CB1-receptor antagonist for the preparation of medicinal products that are useful for helping to quit tobacco consumption.

Families of compounds having affinity for the cannabinoid receptors have been disclosed in several patents and patent applications, in particular European patent application EP-[lacuna] 576 357, which discloses pyrazole derivatives, and patent application WO 96/02248 which discloses in particular benzofuran derivatives.

More particularly, N-piperidino-5-(4-chloro-phenyl)-1-(2,4-dichlorophenyl)-4-methylpyrazole-3-carboxamide, referred to hereinbelow as compound A, of formula:

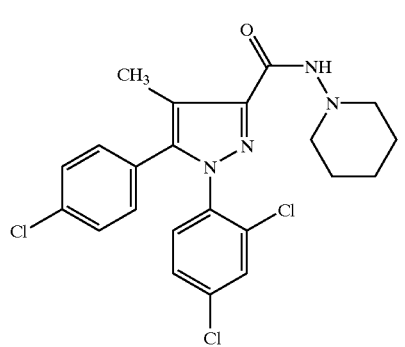

(I)

the pharmaceutically acceptable salts thereof and the solvates thereof are disclosed in European patent EP-[lacuna] 656 354 and by M. Rinaldi-Carmona et al. (FEBS Lett., 1994, 350, 240–244) as being $CB_1$ central-receptor antagonists.

It is disclosed that compound A and its salts, which are central cannabinoid receptor antagonists, may be used to treat appetite disorders, in particular as anorexigenic agents, and in the treatment of disorders associated with the use of psychotropic substances. Furthermore, international patent application WO 99/00119 discloses the use of central cannabinoid receptor antagonists to treat craving disorders, i.e. to control the desire for consumption, in particular for consumption of sugars, carbohydrates, alcohol or drugs and more generally of appetizing ingredients.

It has now been found that compound A, the pharmaceutically acceptable salts thereof and the solvates thereof help in quitting tobacco consumption and are useful in the treatment of nicotine dependence and/or in the treatment of the symptoms of withdrawal from nicotine.

Thus, the administration of compound A, a pharmaceutically acceptable salt or solvate thereof makes it possible to observe, in nicotine consumers such as tobacco smokers, a total or partial abstinence from tobacco, with early or delayed onset. Furthermore, the symptoms of withdrawal from nicotine are very substantially attenuated or even eliminated, and the weight gain after quitting tobacco consumption is reduced or nonexistent.

According to one of its aspects, the present invention relates to the use of N-piperidino-5-(4-chlorophenyl)-1-(2,4-dichlorophenyl)-4-methyl-pyrazole-3-carboxamide, a pharmaceutically acceptable salt thereof or a solvate thereof for the preparation of medicinal products that are useful for helping to quit tobacco consumption, in the treatment of nicotine dependence and/or in the treatment of the symptoms of withdrawal from nicotine.

According to the present invention, compound A, a pharmaceutically acceptable salt thereof or a solvate thereof may also be used, in combination with another active principle, for the preparation of medicinal products that are useful for helping to quit tobacco consumption, in the treatment of nicotine dependence and/or in the treatment of the symptoms of withdrawal from nicotine.

For example, compound A may be combined
- with nicotine, a nicotine agonist or a partial nicotine agonist, or
- with a monoamine oxidase inhibitor (MAOI),
- or with any other active principle which has demonstrated its efficacy in helping to quit tobacco consumption, for example an antidepressant such as bupropion, doxepine, nortriptyline or an anxiolytic agent such as buspirone, or clonidine.

For its use as a medicinal product, compound A, a pharmaceutically acceptable salt thereof or a solvate thereof, alone or in combination with another active principle, must be formulated as a pharmaceutical composition.

Thus, a subject of the present invention is also pharmaceutical compositions containing, in combination, N-piperidino-5-(4-chlorophenyl)-1-(2,4-dichlorophenyl)-4-methylpyrazole-3-carboxamide, a pharmaceutically acceptable salt thereof or a solvate thereof and another active principle, the other active principle being a compound that is useful for helping to quit tobacco consumption and/or that is useful in the treatment of nicotine dependence and/or in the treatment of the symptoms of withdrawal from nicotine. The said other active principle is preferably chosen from:
- nicotine, a nicotine agonist or a partial nicotine agonist, or
- a monoamine oxidase inhibitor (MAOI),
- or any other active principle which has demonstrated efficacy in helping to quit tobacco consumption, for example an antidepressant such as bupropion, doxepine, nortriptyline or an anxiolytic agent such as buspirone, or clonidine.

In the pharmaceutical compositions of the present invention for oral, sublingual, subcutaneous, intramuscular, intravenous, transdermal, local or rectal administration, the active principle, alone or in combination with another active principle, may be administered in unit administration form, as a mixture with conventional pharmaceutical supports, to animals and human beings. The unit administration forms that are suitable comprise oral forms such as tablets, gel capsules, pills, powders, granules, chewing gums and oral solutions or suspensions, sublingual and buccal administration forms, aerosols, implants, local, transdermal, subcutaneous, intramuscular, intravenous, intranasal or intraocular administration forms and rectal administration forms.

In the pharmaceutical compositions of the present invention, the active principle(s) is(are) generally formulated in dosage units. The dosage unit contains 0.5 to 300 mg, advantageously from 5 to 60 mg and preferably from 5 to 40 mg per dosage unit, for daily administrations, one or more times a day.

Although these dosages are examples of average situations, there may be particular cases in which higher or lower dosages are appropriate, and such dosages also form part of the invention. According to the usual practice, the dosage which is appropriate to each patient is determined by the doctor according to the mode of administration, the age, the weight and the response of the said patient.

When a solid composition in the form of tablets is prepared, a wetting agent such as sodium lauryl sulfate may be added to the micronized or non-micronized active principle(s) and the whole may be mixed with a pharmaceutical vehicle such as silica, starch, lactose, magnesium stearate, talc or the like. The tablets may be coated with sucrose, various polymers or other suitable materials or alternatively they may be treated such that they have sustained or delayed activity and such that they continuously release a predetermined amount of active principle.

A preparation in the form of gel capsules is obtained by mixing the active principle(s) with a diluent such as a glycol or a glycerol ester and by incorporating the mixture obtained into soft or hard gel capsules.

A preparation in the form of a syrup or elixir may contain the active principle(s) together with a sweetener, preferably a calorie-free sweetener, methylparaben and propylparaben as antiseptics, and also a flavor enhancer and a suitable colorant.

The water-dispersible powders or granules may contain the active principle(s) as a mixture with dispersants or wetting agents, or suspending agents such as polyvinylpyrrolidone or polyvidone, as well as with sweeteners or flavor enhancers.

For rectal administration, use is made of suppositories which are prepared with binders that melt at the rectal temperature, for example cocoa butter or polyethylene glycols.

Aqueous suspensions, isotonic saline solutions or sterile injectable solutions which contain pharmacologically compatible dispersants and/or solubilizing agents, for example propylene glycol or butylene glycol, are used for parenteral administration.

Thus, to prepare an aqueous solution for intravenous injection, it is possible to use a co-solvent, for example an alcohol such as ethanol or a glycol such as polyethylene glycol or propylene glycol, and a hydrophilic surfactant such as polysorbate 80. To prepare an oily solution for intramuscular injection, the active principle can be dissolved with a triglyceride or a glycerol ester.

Patches in multilaminar form or with a reservoir in which the active principle is in alcoholic solution may be used for transdermal administration.

The active principle(s) may also be formulated in the form of microcapsules or microspheres, optionally with one or more supports or additives.

The active principle(s) may also be in the form of a complex with a cyclodextrin, for example α-, β- or γ-cyclodextrin, 2-hydroxypropyl-β-cyclodextrin or methyl-β-cyclodextrin.

Among the sustained-release forms which are useful in the case of chronic treatments and which may be used are implants. These implants may be prepared in the form of an oily suspension or in the form of a suspension of microspheres in an isotonic medium.

Preferably, compound A is administered orally, as a single dosage intake per day.

According to another aspect of the invention, compound A, a pharmaceutically acceptable salt thereof or a solvate thereof and the other active principle combined may be administered simultaneously, separately or sequentially to help in quitting tobacco consumption.

The expression "simultaneous use" means the administration of the compounds of the composition according to the invention in one and the same pharmaceutical form.

The expression "separate use" means the administration, at the same time, of the two compounds of the composition according to the invention, each in a separate pharmaceutical form.

The expression "sequential use" means the successive administration of the first compound of the composition according to the invention, in one pharmaceutical form, followed by the second compound of the composition according to the invention, in a different pharmaceutical form.

In the case of this "sequential use", the time elapsed between the administration of the first compound of the composition according to the invention and the administration of the second compound of the same composition according to the invention generally does not exceed 24 hours.

The pharmaceutical forms, comprising either only one of the compounds constituting the composition according to the invention or the combination of both compounds, which may be used in the various types of uses described above, may be suitable, for example, for oral, nasal, parenteral or transdermal administration.

Thus, in the case of a "separate use" and of a "sequential use", two different pharmaceutical forms may be intended for the same administration route or for a different administration route (oral and transdermal or oral and nasal or parenteral and transdermal, etc.).

The invention thus also relates to a kit for helping to quit tobacco consumption, containing compound A and another active principle for helping to quit tobacco consumption, in which the said compound A and the said active principle are in separate compartments and in packaging which may be identical or different, and are intended to be administered simultaneously, separately or sequentially. The said active principle is preferably chosen from:

nicotine, a nicotine agonist or a partial nicotine agonist, or a monoamine oxidase inhibitor (MAOI), or any other active principle which has demonstrated efficacy in helping to quit tobacco consumption, for example an antidepressant such as bupropion, doxepine, nortriptyline or an anxiolytic agent such as buspirone, or clonidine.

According to another of its aspects, the invention also relates to a method for helping to quit tobacco consumption, which consists in administering to a nicotine consumer a therapeutically effective amount of compound A, a pharmaceutically acceptable salt thereof or a solvate thereof.

The effects of compound A were studied in rats on a model which predicts the effects on nicotine dependence: the self-administration of nicotine according to W. T. Corrigal and al. Psychopharmacology, 1989, 99, 473–478.

Compound A, administered at a dose of 0.3 mg/kg and 1 mg/kg reduces, in a statistically significant manner, the number of nicotine injections to rats which have learnt to self-administer nicotine intravenously.

Thus, the positive effects of compound A were observed on these two models.

A double-blind study was carried out with individuals who smoked more than 15 cigarettes a day and who showed symptoms of nicotine dependence. The patients received 40 mg of compound A per day for 10 weeks, including 2 weeks before the start of the period of withdrawal from tobacco. A greater level of withdrawal was observed in the treated group than in the group receiving a placebo, in particular during the last 4 weeks of treatment. The withdrawal from tobacco was confirmed by weekly measurement of the levels of carbon monoxide exhaled and of cotinine in the plasma.

EXAMPLE 1

| Gel capsule containing a 5 mg dose of compound A. | |
|---|---|
| Micronized compound A | 5.00 mg |
| Corn starch | 51.00 mg |
| Lactose monohydrate | 99.33 mg |
| Polyvidone | 4.30 mg |
| Sodium lauryl sulfate | 0.17 mg |
| Crosslinked sodium carboxymethylcellulose | 8.50 mg |
| Purified water: qs for wet granulation | |
| Magnesium stearate | 1.70 mg |
| For a filled No. 3 opaque white gel capsule containing | 170 mg |

EXAMPLE 2

| Gel capsule containing a 10 mg dose of compound A. | |
|---|---|
| Micronized compound A | 10.00 mg |
| Corn starch | 51.00 mg |
| Lactose monohydrate | 94.33 mg |
| Polyvidone | 4.30 mg |
| Sodium lauryl sulfate | 0.17 mg |
| Crosslinked sodium carboxymethylcellulose | 8.50 mg |
| Purified water: qs for wet granulation | |
| Magnesium stearate | 1.70 mg |
| For a filled No. 3 opaque white gel capsule containing | 170 mg |

EXAMPLE 3

| Gel capsule containing a 20 mg dose of compound A. | |
|---|---|
| Micronized compound A | 20.00 mg |
| Corn starch | 51.00 mg |
| Lactose monohydrate | 84.33 mg |
| Polyvidone | 4.30 mg |
| Sodium lauryl sulfate | 0.17 mg |
| Crosslinked sodium carboxymethylcellulose | 8.50 mg |
| Purified water: qs for wet granulation | |
| Magnesium stearate | 1.70 mg |
| For a filled opaque white gel capsule containing | 170 mg |

EXAMPLE 4

| Tablet containing a 10 mg dose of compound A. | |
|---|---|
| Micronized compound A | 10.00 mg |
| Corn starch | 50.00 mg |
| 200 mesh lactose monohydrate | 211.50 mg |
| Hydroxypropylmethylcellulose 6 cP | 9.00 mg |
| Sodium carboxymethylstarch | 15.00 mg |
| Sodium lauryl sulfate | 1.50 mg |
| Magnesium stearate | 3.00 mg |
| Purified water: qs | |
| For a finished tablet containing | 300 mg |

EXAMPLE 5

| Tablet containing a 30 mg dose of compound A. | |
|---|---|
| Micronized compound A | 30.00 mg |
| Corn starch | 80.00 mg |
| 200 mesh lactose monohydrate | 252.00 mg |
| Povidone K 30 | 12.00 mg |
| Crosslinked sodium carboxymethylcellulose | 20.00 mg |
| Sodium lauryl sulfate | 2.00 mg |
| Magnesium stearate | 4.00 mg |
| Purified water: qs | |
| For a finished tablet containing | 400 mg |

What is claimed is:

1. A method for quitting tobacco consumption, the treatment of nicotine dependence and/or the treatment of the symptoms of withdrawal from nicotine which comprises administering to a patient in need of such treatment an effective amount of N-piperidino-5-(4-chlorophenyl)-1-(2,4-dichlorophenyl)-4-methylpyrazole-3-carboxamide, a pharmaceutically acceptable salt thereof or a solvate thereof.

2. A method according to claim 1 wherein N-piperidino-5-(4-chlorophenyl)-1-(2,4-dichlorophenyl)-4-methylpyrazole-3-carboxamide, a pharmaceutically acceptable salt thereof or a solvate thereof is administered in combination with another active principle, in which the other active principle is useful for helping to quit tobacco consumption and/or useful in the treatment of nicotine dependence and/or useful in the treatment of withdrawal from nicotine.

3. A pharmaceutical composition containing, in combination, N-piperidino-5-(4-chlorophenyl)-1-(2,4-dichlorophenyl)-4-methylpyrazole-3-carboxamide, a pharmaceutically acceptable salt thereof or a solvate thereof and another active principle in which the other active principle is useful for helping to quit tobacco consumption and/or useful in the treatment of nicotine dependence and/or in the treatment of the symptoms of withdrawal from nicotine.

4. The pharmaceutical composition as claimed in claim 3, containing N-piperidino-5-(4-chlorophenyl)-1-(2,4-dichlorophenyl)-4-methylpyrazole-3-carboxamide, a pharmaceutically acceptable salt thereof or a solvate thereof and nicotine, a nicotine agonist or a partial nicotine agonist.

5. The pharmaceutical composition as claimed in claim 3, containing N-piperidino-5-(4-chlorophenyl)-1-(2,4-dichlorophenyl)-4-methylpyrazole-3-carboxamide, a pharmaceutically acceptable salt thereof or a solvate thereof and a monoamine oxidase inhibitor.

6. A method according to claim 1 for quitting tobacco consumption.

7. A method according to claim 1 for the treatment of nicotine dependence.

8. A method according to claims 1 for the treatment of the symptoms of withdrawal from nicotine.

9. A method according to claim 6 wherein N-piperidino-5-(4-chlorophenyl)-1-(2,4-dichlorophenyl)-4-methylpyrazole-3-carboxamide, a pharmaceutically acceptable salt thereof or a solvate thereof is administered in combination with another active principle which is useful in helping to quit tobacco consumption.

10. A method according to claim 7 wherein N-piperidino-5-(4-chlorophenyl)-1-(2,4-dichlorophenyl)-4-methylpyrazole-3-carboxamide, a pharmaceutically acceptable salt thereof or a solvate thereof is administered in combination with another active principle which is useful in the treatment of nicotine dependence.

11. A method according to clam 8 wherein N-piperidino-5-(4-chlorophenyl)-1-(2,4-dichlorophenyl)-4-methylpyrazole-3-carboxamide, a pharmaceutically acceptable salt thereof or a solvate thereof is administered in combination with another active principle which is useful in the treatment of withdrawal from nicotine.

* * * * *